United States Patent [19]
Webster, Jr.

[11] Patent Number: 5,057,092
[45] Date of Patent: Oct. 15, 1991

[54] BRAIDED CATHETER WITH LOW MODULUS WARP

[76] Inventor: Wilton W. Webster, Jr., 1388 Crest Dr., Altadena, Calif. 91001

[21] Appl. No.: 504,298

[22] Filed: Apr. 4, 1990

[51] Int. Cl.⁵ ............................................. A61M 25/00
[52] U.S. Cl. ..................... 604/282; 604/114; 128/658; 138/123
[58] Field of Search ............... 604/282, 280, 281, 260, 604/114; 128/658; 87/5, 6, 8; 138/123, 127

[56] References Cited

U.S. PATENT DOCUMENTS

| | | | |
|---|---|---|---|
| 2,268,321 | 12/1941 | Flynn | 604/282 |
| 3,416,531 | 12/1968 | Edwards | 604/282 |
| 3,452,742 | 7/1969 | Muller | |
| 3,498,286 | 3/1970 | Polanyi et al. | 604/282 |
| 3,552,384 | 1/1971 | Pierie et al. | |
| 3,631,848 | 1/1972 | Muller | |
| 3,924,632 | 12/1975 | Cook | 604/282 |
| 4,033,331 | 7/1977 | Guss et al. | |
| 4,245,624 | 1/1981 | Komiya | |
| 4,447,239 | 5/1984 | Kritten | 604/282 |
| 4,456,017 | 6/1984 | Miles | |
| 4,603,705 | 8/1986 | Speicher et al. | |
| 4,632,842 | 12/1986 | Karwoski et al. | |
| 4,633,880 | 1/1987 | Osypka et al. | |
| 4,651,751 | 3/1987 | Swendson et al. | |
| 4,682,596 | 7/1987 | Bales et al. | |
| 4,817,613 | 4/1989 | Jaraczewski | 604/282 |
| 4,832,048 | 5/1989 | Cohen | |
| 4,898,591 | 2/1990 | Jang et al. | 604/282 |

FOREIGN PATENT DOCUMENTS 2501995  9/1982  France .

Primary Examiner—John D. Yasko
Assistant Examiner—Kathleen A. Daley
Attorney, Agent, or Firm—Christie, Parker & Hale

[57] ABSTRACT

An intravascular catheter comprises an elongated catheter body having a flexible plastic inner wall, a braided reinforcing mesh surrounding the inner wall and a flexible plastic outer wall surrounding the reinforcing mesh. The braided reinforcing mesh comprises helical members having a high modulus of elasticity and longitudinal warp members having a lower modulus of elasticity.

7 Claims, 2 Drawing Sheets

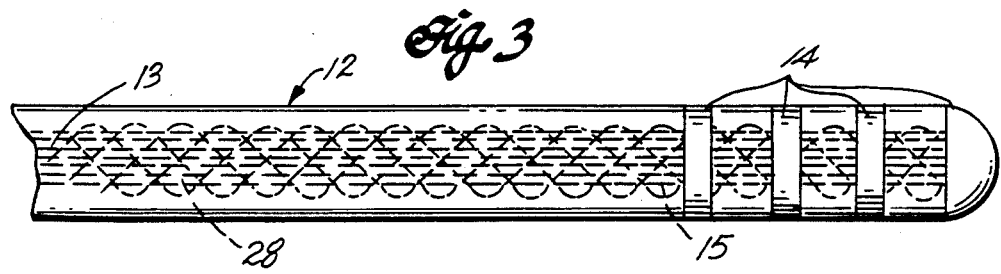
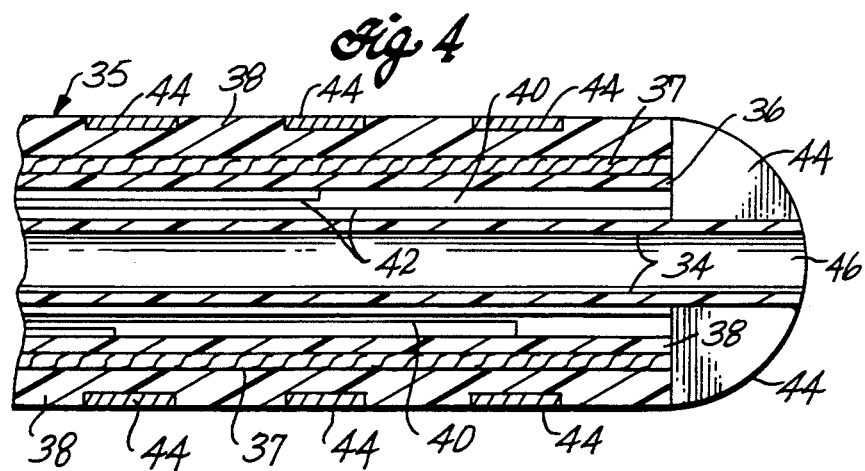
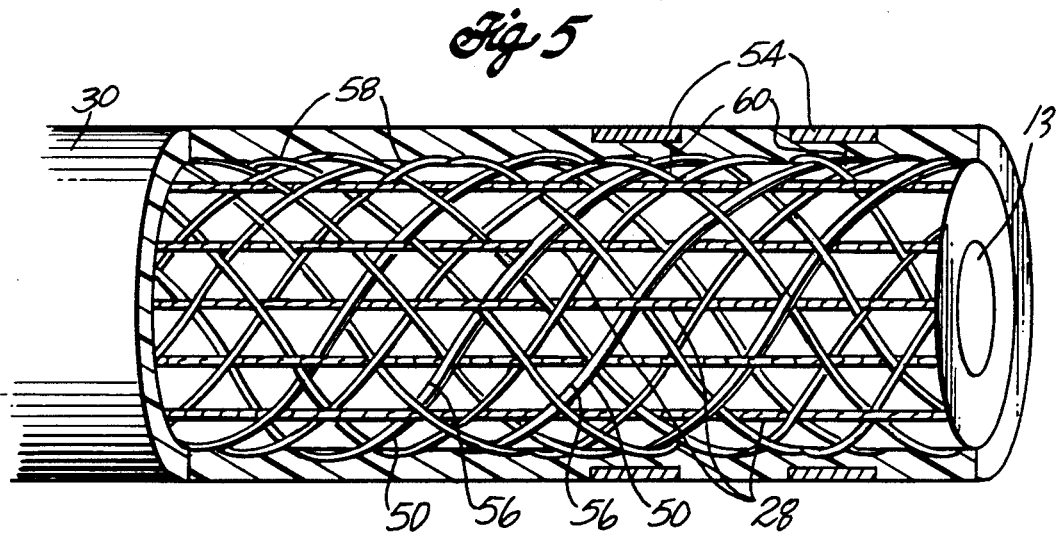

BRAIDED CATHETER WITH LOW MODULUS WARP

FIELD OF THE INVENTION

This invention relates to intravascular catheters and more particularly to an intravascular catheter having a reinforcing mesh comprising helical braid members having a high modulus of elasticity and axial warp members having a low modulus of elasticity.

BACKGROUND OF THE INVENTION

Cardiovascular electrode catheters are used to electrically stimulate and/or monitor the heart and, in some cases, to modify heart tissue. Such cardiovascular catheters typically comprise an elongated tubular catheter body with one or more electrodes mounted at the distal end of the catheter body. Wires extend from the electrodes through the catheter body to a connector at the proximal end of the catheter body. The connector can be plugged into an electrical stimulator and/or recorder or other source of electrical energy.

The catheter bodies of such cardiovascular catheters are typically made of an inner plastic tube surrounded by and reinforced with a braided stainless steel mesh An outer plastic sleeve covers the reinforcing mesh. Such constructions generally provide high torsional stiffness, high resiliency and high flexibility, i.e. are easily bendable In fact, the resulting catheter is usually more flexible in bending than is generally desirable.

Employing less flexible plastic tends to reduce undesirable bending flexibility. However, catheters tend to lose resiliency by increasing the hardness of the plastic Accordingly, there is a need for a catheter construction which controls flexibility while maintaining resiliency.

SUMMARY OF THE INVENTION

The present invention provides an intravascular catheter which exhibits high torsional stiffness and high bending stiffness while maintaining high resiliency. Catheters of the present invention comprise an elongated tubular body. The tubular body comprises a plastic inner wall, a reinforcing braided mesh in surrounding relation to the inner wall and a plastic outer wall in surrounding relation to the reinforcing mesh.

The mesh comprises braided helical members having a high modulus of elasticity Preferred helical braid members are made of stainless steel. Interwoven into the braided helical members are longitudinal warp members having a modulus of elasticity considerably lower than that of the helical members, preferably at least one order of magnitude lower than the helical members. A presently preferred warp member for use with stainless steel helical members is made of dacron.

The presence of low modulus warp members increases the bending stiffness of the catheter without decreasing the resiliency of the catheter body.

BRIEF DESCRIPTION OF THE DRAWINGS

These and other features and advantages of the present invention will be better understood by reference to the following detailed description when considered in conjunction with the accompanying drawings wherein:

FIG. 3 is a side view of the distal end of another cardiovascular electrode catheter embodying the invention;

FIG. 4 is a side cross sectional view of an open lumen cardiovascular electrode catheter embodying the invention; and FIG. 5 is a side cut-away view of the distal end of a cardiovascular electrode catheter showing another preferred embodiment of the invention.

DETAILED DESCRIPTION OF THE DRAWINGS

Figure 1:
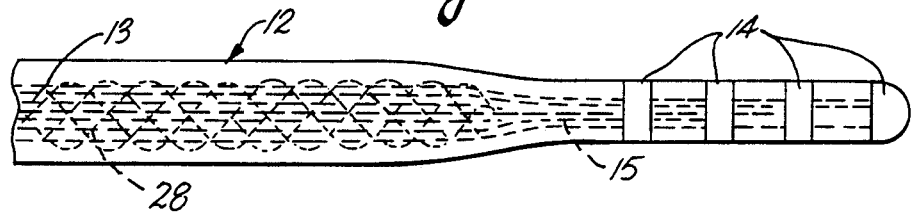
FIG. 1 is a side view of the distal end of a cardiovascular electrode catheter embodying the invention.

The present invention is particularly useful in the construction of cardiovascular electrode catheters. With reference to FIG. 1, there is shown a closed lumen cardiovascular electrode catheter which comprises an elongated tubular body 12 having a central lumen 13. At the distal end of the body 12 are a plurality of spaced apart electrodes 14. Wires 15, connected to the electrodes 14, extend through the lumen of the catheter body to a handle or connector (not shown) which can be plugged into an electrical stimulator and/or recorder or the like. An example of such a catheter is more fully described in U.S. patent application Ser. No. 273,048, filed Nov. 18, 1988, which is incorporated herein by reference.

Figure 2:
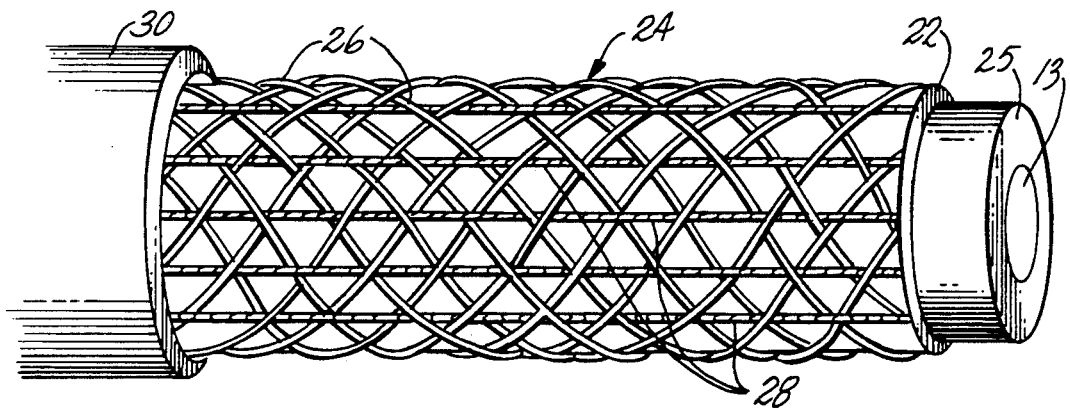
FIG. 2 is a side cut-away view of a catheter body constructed in accordance with the present invention.

With reference to FIG. 2, the tubular catheter body 12 comprises an inner wall 22, a braided reinforcing mesh 24, surrounding the inner wall 22, and an outer wall 30 surrounding the braided reinforcing mesh 24. The inner and outer walls 22 and 30 are made of a flexible plastic material such as polyurethane In the embodiment shown, a nylon sleeve 25 extends through the lumen 13 to increase bending stiffness of the catheter.

The braided reinforcing mesh 24 comprises interwoven helical braid members 26 and longitudinal warp members 28. The reinforcing mesh typically comprises 12, 16 or 24 interwoven helical members, half extending in one direction and the other half extending in the counter direction. The reinforcing mesh also comprises 6, 8 or 12 warp members respectively, the number of warp members being half the number of helical members.

The tightness or angle of the helical members 26 to the longitudinal members 28 is not critical but is preferably from about 30° to about 45°. An angle less than about 30° is not preferred because as the braid angle becomes smaller, the catheter tends to buckle when it is bent. Further, such catheters tend not to transmit torque around corners as well as catheters having higher braid angles. Braid angles greater than 45° are not preferred because they do not appear to offer any advantage and are less economical.

The helical members 26 are made of a material having a high modulus of elasticity. Preferred helical members are made of stainless steel wire, although, depending on the application, materials such as kevlar thread and Specter Fiber, a modified polyethylene material marketed by Allied Signal, may be used. Warp members 28 are made of a material having a lower modulus of elasticity, preferably less than $10^6$ and preferably at least one order of magnitude less than that of the helical members. This is to assure that the elastic limit of the warp members will not be exceeded when the catheter is bent during use. Dacron warp members are presently preferred for use with stainless steel helical members. Nylon warp members are preferred for use with kevlar or Spector Fiber helical members.

The longitudinal warp members of the reinforcing mesh increase the bending stiffness of the catheter body. This reduces the criticality of the wall thickness and hardness of the inner tube and outer sleeve and, if desired, allows the use of smaller wall thicknesses and/or softer materials for the inner tube and outer sleeve.

The reinforcing mesh is made by a conventional braiding process. In such a process, the braid members are interwoven, under tension, around the inner wall. The outer wall is then applied by dipping, spraying, extrusion or any other suitable process.

The inner and outer diameters of the catheter body 12 as well as the diameters of the helical and warp members will depend on the particular application. For example, the lumen for cardiovascular electrode catheters must be sufficiently large to accommodate the copper electrode leads which extend from the electrodes to the stimulator or recorder plus a safety wire which is typically attached to the tip electrode. The electrode leads typically have a diameter of 0.005 inch and the safety wire typically has a diameter of 0.0075 inch.

For closed lumen cardiovascular electrode catheters having a French size 6 and having four electrodes, it is presently preferred that the catheter body have an inner diameter of about 0.047 inch and an outer diameter of about 0.078 inch. It is also preferred that a nylon stiffening tube, having an inner diameter of 0.030 inch, line the inner wall of the catheter body. In this embodiment, the stainless steel wire which forms the braided reinforcing mesh has a diameter of approximately 0.0026 inch. The dacron warp members comprise multiple filaments which tend to flatten out against the stainless steel helical members. This is desirable because it minimizes the increase in wall thickness due to the reinforcing braided mesh.

In the embodiment shown in FIGS. 1 and 2, the distal tip is tapered slightly and the reinforcing mesh does not extend all the way to the distal tip. Such a construction provides a maximum flexibility, but reduced tortional stiffness at the distal tip. It is understood that the invention is equally applicable to catheter construction, as shown in FIG. 3 wherein the reinforcing mesh extends fully to the distal tip.

The invention is also equally applicable to open lumen type catheters such as that shown in FIG. 4. The catheter body 35 again comprises an inner wall 36, a reinforcing mesh 37 and an outer wall 38. In such a catheter, a nylon inner tube 34 is spaced apart from the inner wall of the catheter body 35 to provide an annular lumen 40 for carrying the copper electrode lead wires 42 from the electrodes 44. The central lumen 46 is open at the distal end to enable substances to be passed through the catheter. For example, open lumen catheters are used for injecting substances into the blood vessels, for taking samples from the blood vessels, or even for inserting optical fibers or the like into the blood vessel downstream of the catheter to perform some procedure.

In a particularly preferred embodiment of the invention, as shown in FIG. 5, the electrode lead wires 50 are built into the braided reinforcing mesh. In such an embodiment, the copper lead wires 50 run along the side of separate helical members 56. The lead wires 50 all extend in one helical direction to avoid crossing each other. It is preferred that the helical members 58 extending in the counter direction be non-conductive, e.g. made of kevlar, specter fiber or the like which allows the use of uninsulated lead wires At the distal end of the catheter, the electrode lead wires 50 are exposed and electrically connected to the electrodes 54. In the embodiment shown in FIG. 5, a short piece of cooper wire 60 is looped under and soldered to the electrode lead 50 at one end and electrically connected, e.g. soldered to the electrode 54 at its opposite end.

An arrangement wherein the electrode leads are built into the braided reinforcing mesh enables the use of smaller diameter electrode catheters which provides the advantage that the catheter may then be inserted into the patient through a smaller introducer. For open-lumen catheters, such an arrangement also provides a larger lumen for a particular catheter size The preceding description has been presented with reference to the preferred embodiments of the invention shown in the accompanying drawings Workers skilled in the art and technology to which this invention pertains will appreciate the alterations and changes in the described apparatus can be practiced without meaningfully departing from the principals spirit and scope of the invention.

Accordingly, the foregoing description should not be read as pertaining only to the precise structures and apparatus described, but rather should be read consistent with and as support for the following claims which are to have their fullest fair scope.

I claim:

1. An intravascular catheter construction comprising:
   a flexible inner tube;
   a braided reinforcing mesh in surrounding relation to the inner tube, said reinforcing mesh comprising interwoven helical members and longitudinal warp members, said warp members comprising a lower modulus of elasticity than the helical members; and
   a flexible plastic outer sleeve in surrounding relation to the reinforcing mesh.

2. An intravascular catheter construction as claimed in claim 1 wherein the warp members comprise a modulus of elasticity of less than $10^6$.

3. An intravascular catheter construction as claimed in claim 1 wherein the warp members comprise a modulus of elasticity of at least one order of magnitude less than the modulus of elasticity of the helical members.

4. An intravascular catheter construction as claimed in claim 1 wherein the helical members are made of stainless steel and the warp members are made of dacron.

5. An intravascular catheter construction as claimed in claim 1 wherein the helical members are made of kevlar and the warp members are made of nylon.

6. An intravascular electrode catheter comprising:
   an elongated tubular catheter body having an inner wall, a braided reinforcing mesh in surrounding relation to the inner wall and an outer wall in surrounding relation to the reinforcing mesh, said reinforcing mesh comprising first helical members extending in one helical direction and second helical members extending in the opposite helical direction and interwoven with the first helical members and further comprising at least two electrode lead wires extending adjacent separate first helical members and interwoven with said second helical members;
   at least two electrodes mounted at the distal end of the catheter body; and
   means for electrically connecting each electrode to a separate electrode lead in the reinforcing mesh.

7. An intravascular electrode catheter comprising:

an elongated tubular catheter body having an inner wall, a braided reinforcing mesh in surrounding relation to the inner wall and an outer wall in surrounding relation to the reinforcing mesh, said reinforcing mesh comprising first helical members extending in one helical direction and second helical members extending in the opposite helical direction and interwoven with the first helical members wherein said second helical members are made of an electrically nonconductive material and wherein said first helical members comprise at least two electrode lead wires interwoven with and maintained in electrical separation by said second helical members;

at least two electrodes mounted at the distal end of the catheter body; and means for electrically connecting each electrode to a separate electrode lead in the reinforcing mesh.

* * * * *